United States Patent [19]

Hunter et al.

[11] 4,136,119
[45] Jan. 23, 1979

[54] M-MENTHENONE AND PROCESS FOR ITS PRODUCTION

[75] Inventors: George L. K. Hunter; Benjamin C. Clark, Jr., both of Atlanta, Ga.

[73] Assignee: The Coca-Cola Company, Altanta, Ga.

[21] Appl. No.: 865,829

[22] Filed: Dec. 30, 1977

[51] Int. Cl.$^2$ .................. C07C 45/00; C07C 45/22
[52] U.S. Cl. ..................... 260/586 R; 260/590 C; 260/348.54; 260/348.39; 260/348.25
[58] Field of Search ........... 260/586 R, 586 P, 348 C, 260/590 C

[56] References Cited

U.S. PATENT DOCUMENTS

| | | | |
|---|---|---|---|
| 1,477,691 | 12/1923 | Callsen | 260/586 R |
| 2,619,504 | 11/1952 | Bibb et al. | 260/586 R |
| 2,619,504 | 11/1952 | Bibb et al. | 260/586 R |
| 2,790,708 | 7/1957 | Oakley et al. | 260/593 R |
| 2,887,479 | 5/1959 | Heseltine | 260/240 |
| 2,918,495 | 12/1959 | Booth | 260/586 R |
| 3,009,959 | 11/1961 | Heath et al. | 260/593 R |
| 3,151,167 | 9/1964 | Eisenmann et al. | 260/586 R |
| 3,397,120 | 8/1968 | Diana et al. | 203/28 |
| 3,531,528 | 9/1970 | Ledmar et al. | 260/590 C |
| 3,538,164 | 11/1970 | Leffingwell et al. | 260/586 R |
| 3,560,571 | 8/1972 | Kropp | 252/522 |
| 3,734,930 | 5/1973 | Razdam et al. | 260/345.3 |
| 3,814,733 | 6/1974 | Bledsoe et al. | 260/631.5 |
| 3,927,107 | 12/1975 | Schulte-Elte et al. | 260/586 R |
| 3,928,456 | 12/1975 | Kovats et al. | 260/586 R |

OTHER PUBLICATIONS

Kraus et al., "Tetra. Lett.", 1977(1), 13–16.
Beilstein, "Hand. Der Org. Chem.", E III, vol. VII, p. 256.
Stork et al., "J.A.C.S.", 85, 207 (1963).
Huang et al., "J.A.C.S.", 95, 1936 (1973).
Konst et al., "Int. Flav. Food Addit", 6(2) 121 (1975).
Gloor et al., "Helv. Chim. Acta.", 1974, 57(6) 1815–1845.
Zimmerman et al., "J.A.C.S.", 97, 5497–5507 (1975).
Villorelli et al., "Helv. Chim. Acta.", 1975, 58(5), 1379–1425.
Ficini et al., "Tetra Letters", 1976, (9), 679–682.
Ohloff et al., "Helv. Chim. Acta.", 51, 1328 (1968).
Arata et al., "Tetra Letters", 1976, 3861.
Josli et al., "Tetra", 27, 475 (1971).
Settine et al., "J. Org. Chem.", 32, 2910 (1967).
Arbuzov et al., "Dokl. Akad. Nauk SSSR", 204(5), 1115–1117 (1972).
Anderson et al., "J. Org. Chem.", 38, 2267 (1973).
Arbuzov et al., "Izv. Akad. Nauk SSSR Ser Khim", 2163 (1969).
Settine et al., "J. Org. Chem.", 29, 616 (1964).
Apsmon, "Total Syn. of Nat. Products", p. 54 (1973).
Simonsen, "The Terpenes", 2nd Edition, vol. 2, pp. 95–99 (1949).

*Primary Examiner*—Norman Morgenstern
*Attorney, Agent, or Firm*—Michael J. Gilroy

[57] ABSTRACT

A m-Menthenone, 2-Methyl-4-siopropylcyclohex-3-en-1-one, (MICO) which possesses a cooling fragrance, is described. This compound or any one of a family of alkyl substituted analogs may be synthesized by a Lewis acid catalyzed rearrangement of 2,3-epoxycarane or its theoretically obtainable alky, substituted analogs.

35 Claims, No Drawings

M-MENTHENONE AND PROCESS FOR ITS PRODUCTION

BACKGROUND OF THE INVENTION

This invention is related to a m-Menthenone, and to a general process for the synthesis of certain cyclohex-3-en-1-ones.

As is well known, terpenes, in general, have long been recognized as odoriferous components in fragrance compositions. Because of their great importance to the fragrance industry, monoterpenes having a basic molecular formula of $C_{10}H_{16}$ have been extensively studied, and numerous such terpenes and their alcohol, ketone aldehyde, and esters derivatives dot the scientific literature. Shown in Table I are representative examples of cyclohexenones, together with their publication citations, which are most pertinent to the present invention.

Table I discloses that Kraus and Zartner have synthesized the compound 2-methyl-4-isopropylcyclohex-3-en-1-one (MICO), based on instrumental data from NMR performed in carbon tetrachloride at 6 Hz (which shows a nine hydrogen doublet at tau=8.98 (J = 6 Hz) and a single hydrogen multiplet at tau=4.30), a mass spectrum (which shows a peak for the molecular ion at 152) and an infrared spectrum (which shows a carbonyl peak at 1750 reciprocal centimeters and an ethylenic unsaturation peak at 1645 reciprocal centimeters).

TABLE I
REPRESENTATIVE CYCLOHEXENONES

| Structural Formula | Reference |
|---|---|
| | U.S. Pat. No. 2,918,495 to Booth |
| | Beilstein, "Handbuch Der Organischen Chemie," Vol. VIII, & III p. 256 |
| | Stork, et. al., J. Am. Chem. Soc., 85, 207, (1963). |
| | Huang, et. al., J. Am. Chem. Soc., 95, 1936–44 (1973); C.A. 78:135394n. |
| | Konst, et. al., Int. Flavours and Food Addit., 6 (2), 121 (1975). |
| | U.S. Pat. No. 3,397,120 to Diana et. al. |
| | U.S. Pat. No. 2,619,504 to Bibb, et. al. |
| | U.S. Pat. No. 2,887,479 to Heseltine |
| | U.S. Pat. No. 3,560,571 to Kropp |
| | U.S. Pat. No. 3,538,164 to Leffingwell, et. al. |
| CH(OMe)₂ | Gloor, et. al., Helv. Chim. Acta, 1974, 57(6), 1815–45; C.A. 82:24283p |

TABLE I-continued
REPRESENTATIVE CYCLOHEXENONES

| Structural Formula | Reference |
|---|---|
| φ | Zimmerman, et. al., J. Am. Chem. Soc., 97, 5497–5507, (1975); C.A. 83:163382d |
| (R=Me or phenyl) | Villorelli, et al., Helv. Chim. Acta, 1975, 58(5), 1379–425; C.A. 84:583036 |
| (R=1-(diethylamino) | Ficini, et. al., Tetrahedron Lett., 1976, (9), 679–82; C.A. 85:204755 |
| propylidene | Kraus and Zartner, Tetrahedron Lett., 1977 (1), 13–16; G. Zartner, Dissertation, Universitat Tubingen, 1975. |

U.S. Pat. No. 3,538,164 to Leffingwell discloses that limonene 1,2-epoxide produces dihydrocarvone when treated with perchloric acid in an inert solvent, and that dihydrocarvone readily isomerizes to p-menth-3-en-2-one, according to the following reaction:

U.S. Pat. No. 3,560,571 to Kropp teaches that 3,4-epoxycarane (synthesized from 3-carene and a peracid) produces 4-caranone and p-menth-3-en-2-one when treated with Lewis acids such as zinc salts in a reaction medium such as benzene, according to the following reaction:

U.S. Pat. No. 3,814,733 to Bledsoe, et al., discloses that 2,3-epoxycarane (1) rearranges to 1-methyl-(1-methylethenyl)-cyclohex-2-en-1-ol (2) when treated with metatitanic acid, i.e., It has also been reported (Ohloff and Giersch, Helv. Chim. Acta, 51, 1328 (1968)) that epoxidation of 2,3-carene with peracetic acid leads directly, after saponification of acetates, to 1-methyl-4-(1-methylethenyl)-cyclohex-2-en-1-ol (2) and its hydrated derivative (3), i.e.,

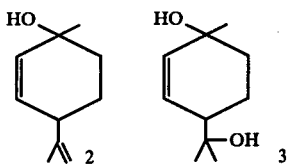

Recent work by Arata, et al., (Tetrahedron Lett., 1976, 3861) has yielded findings, consistent with earlier results, showing that 2,3-epoxycarane undergoes rearrangement to the same 1-methyl-4(1-methylethenyl)-cyclohex-2-en-1-ol, and alcohols and hydrocarbons derived most likely therefrom, when reacted in the presence of solid acids and bases such as $SiO_2$-$Al_2O_3$, $Al_2O_3$, $FeSO_4$, $TiO_2$-$ZrO_2$ and CaO. Conversely, however, Arata, et al., found that 3,4-epoxycarane (4) gave relatively good yields of a ring contraction product, aldehyde (5) (along with ketones and allylic alcohols, almost all of which could be derived from an intermediate of type 6), when treated with the same solid acids and bases, according to the following reaction:

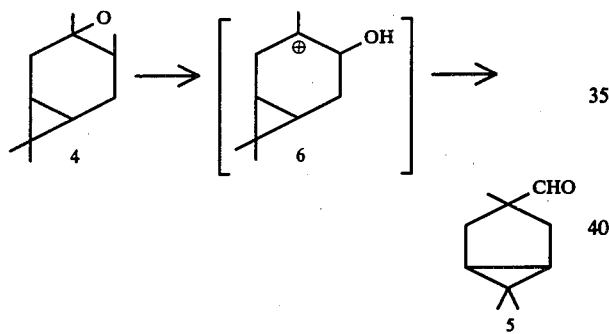

Findings by Joshi, et al. (Tetrahedron, 27, 475 (1971)) and Settine, et al., (J. Org. Chem., 32, 2910 (1967)) have shown that such ring contraction products are also produced by $ZnBr_2$ catalysis of the 3,4-epoxycarane rearrangment.

Finally, Arbuzov, et al. (Doklady Akademii Nauk SSSR, 204(5), 1115-1117 (1972)) have published that 2,3-epoxycarane, when isomerized with zinc bromide in benzene, yields the following:

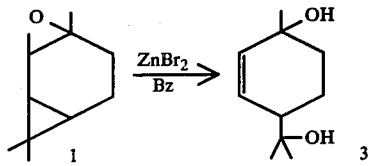

Thus, while it would be desirable to be able to obtain 2-methyl-4-isopropylcyclohex-3-en-1-one (MICO) or its alkyl substituted derivatives from 2,3-epoxycarane by a single step synthetic route, no such teaching may be found in the prior art.

SUMMARY

It has now been found that 2-methyl-4-isopropylcyclohex-3-en-1-one (MICO) may be prepared in one reactive step from 2,3-epoxycarane by Lewis acid-catalyzed rearrangement in an inert organic solvent by (a) dissolving the 2,3-epoxycarane in the solvent to form a first reactant mixture, (b) mixing the Lewis acid in said solvent to form a second reactant mixture, and (c) combining the first reactant mixture with the second reactant mixture for a time sufficient for the MICO to form. It is believed that certain alkyl substituted derivatives of 2,3-epoxycarane would undergo similar rearrangement to yield analogously substituted cyclohex-3-en-1-ones.

DETAILED DESCRIPTION OF THE INVENTION

A complete understanding of the present invention will be gained by those skilled in the art from the description and representative examples given below.

For the purposes of this disclosure, the following structures with associated numbering of the cyclohexene skeleton will be used, i.e.,

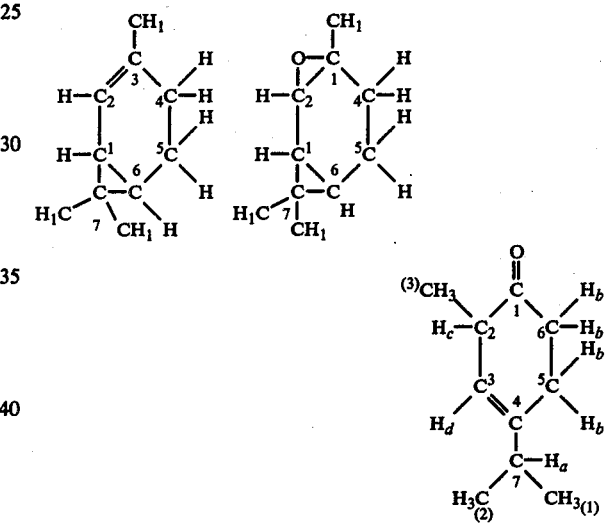

Analyses by VPC were performed on a Perkin-Elmer 900 equipped with dual 12 ft. ⅛ in. I.D. glass columns, modified for on-column injection and packed with 5% Triton X 305 on Chromosorb W. H. P. 80-100 mesh. The oven temperature was programmed from 70° C to 170° C at 2°/min. A flow rate of 35 mL/min of helium was employed. Compounds were purified as clear liquids by collection in glass capillaries or ⅛ in. glass tubing from an F&M 810 GC equipped with a TC detector, ¼ in. glass column and generally operated as above. IR spectra were determined using a PE-221 or PE-281; and MS were determined using a Hitachi-RMU-6L. NMR were determined on a Varian T-60-A or JEOL-MH-100 in $DCCl_3$ using $Me_4Si$ as an internal standard. Microanalysis was performed by Spang Microanalytical Laboratory, Ann Arbor, Mich.

The parent compound, 2,3 carene, shown above was selected for use in the process of this invention due to the ready availability of the starting materials. Nevertheless, as further discussed below, such choice is not intended to limit the utility of the process to 2,3-carene.

2,3-carene (contaminated with approximately 2% 3,4-carene) was oxidized by the method of Anderson and Veysoglu (J. Org. Chem., 38, 2267 (1973)) using m-chloroperbenzoic acid in a two phase system to give an essentially quantitative yield of 2,3-epoxycarane. Experimental details and characterization criteria are shown in Example I.

EXAMPLE I

Preparation and Characterization of 2,3-Epoxycarane m-Chloroperbenzoic acid (1.28 g, 6.3 mmol) was added over 1.5 h to a mixture of 0.75 g (5.5 mmol) of 2,3-carene, 18 mL of 0.5 M $NaHCO_3$ and 60 mL of $CH_2Cl_2$, stirred in an ice bath. The ice bath was then removed and the mixture stirred an additional 2 h. The solution was washed with saturated $NaHCO_3$ (2 × 20 mL), $H_2O$ (1 × 20 mL) and saturated NaCl (1 × 20 mL), dried over anhydrous potassium carbonate and concentrated under reduced pressure to yield epoxide 1 (0.8 g). VPC analysis showed the material to be over 95% pure and it was used without further purification. IR (neat) 2940, 1450, 1372 and 855 reciprocal centimeters; NMR PPM 0.6 (board, M, 1H) and 1.0 (n, M, 1H), (cyclopropyl protons), 1.07 (s, 6H, $CH_3$—C—$CH_3$), 1.27 (s, 3H, $CH_3$—C—O), 1.67 (t, 2H superimposed on br, M, 2H, —$CH_2$—$CH_2$), 3.0 (d, 1H, J=2Hz, H—C—O); MS m/e (rel. intensity) 152(7), 134(73), 132(19), 120(20), 119(100), 117(34), 91(67), 79(15), 77(23). The NMR of the 2,3-epoxycarane produced by this method compared well with the spectrum published by Arbuzov, et. al. (Izr. Akad. Nauk, SSSR, Ser. Khim., 2163 (1969)). A conventional procedure using monoperphthalic acid gave considerable rearrangement to 1-methyl-4-(1-methylethynyl)-cyclohex-2-en-1-ol (2) and its hydrated derivative (3).

Treatment of 2,3-epoxycarane with the Lewis acid zinc bromide in refluxing toluene yielded a product solution containing MICO, amounting to approximately 40% of the volatile products as determined by VPC, together with a number of other terpene hydrocarbons. The experimental procedure used is described in Example II.

EXAMPLE II

Rearrangement of 2,3-Epoxycarane With $ZnBr_2$

Approximately 20 mg of $ZnBr_2$ (Fisher Certified-not fused) was added to 3 mL of toluene which had been distilled and stored over molecular sieves. The mixture was brought to reflux with vigorous stirring (to disperse the solid zinc bromide) in an apparatus which had been well flushed with nitrogen and equipped with a drying tube. Three quarters of a mixture of 2,3-epoxycarane (150 mg, 0.98 mmol) and 3 mL of toluene was added immediately. After 10 min the remaining one quarter was added over a 10 min period. Forty minutes after initial oxide addition the reaction mixture was cooled, taken up in 30 mL of ether, washed successively with water (2 × 10 mL), saturated $NaHCO_3$ (1 × 10 mL), saturated NaCl (1 × 10 mL) and dried over anhydrous $Na_2SO_4$. Partial removal of solvent under reduced pressure afforded an oily residue from which 2-methyl-4-isopropylcyclohex-3-en-1-one (MICO) was isolated by preparative VPC. IR ($CCl_4$) 2975, 1720, 1360, 1200, 1180(d), 970 and 930 reciprocal centimeters; UV (95% EtOH) lambda (max) 290 nm (extinction coefficient = 90.9); NMR ($DCCl_3$) PPM 1.04 (d, 6H, J = 7 Hz, $CH_3$—C—$CH_3$), 1.14 (d, 3H, J = 7 Hz, $CH_3$—C—), 2.3 (quintet, 1H, J = 7 Hz), 2.46 (n, M, 4H), 2.88 (br, Q with additional splitting H—C—C=O), 5.37 (n, M, 1H, H—C=C); MS m/e (rel. intensity) 153(4), 152(42), 135(5), 100(65), 109(10), 96(11), 95(100), 81(30), 68(10), 67(25), 55(11). Anal. calcd. for $C_{10}H_{16}O$: C, 78.89; H, 10.59. Found: C, 79.08; H, 10.41. An IR of the major product of the reaction showed a peak at 1720 reciprocal centimeters, attributed to the presence of a nonconjugated carbonyl. The product MICO exhibited a cool, refreshing menthol fragrance with a slight raspberry note which finds utility for the compound in odorant compositions.

The procedure of Example II was essentially repeated substituting benzene for toluene as the solvent with the result that the yield of MICO was reduced from approximately 40% of total volatiles to approximately 30%. Using a procedure similar to that of Example II, but with the substitution of approximately 2 wt. percent tin tetrachloride in benzene for zinc bromide in toluene and cooling the reaction to approximately 5° C in an ice bath rather than refluxing, the yield of MICO was further reduced to approximately 20%. MICO isolated from these latter two synthetic preparations was characterized by comparison to the compound prepared in Example II.

Table II shows the reaction products and amounts as they elute from the VPC for the three exemplary synthetic routes.

The 100-MHZ NMR spectrum of the reaction product thought to be MICO was in accord with that theoretically predicted. The compound spectrum exhibited a sharp 6-proton doublet at 1.04 (J = 7 Hz; $CH_3$, 1 and 2), a 3-proton doublet at 1.14 (J = 7 Hz; $CH_3(3)$), a 1-proton quintet centered at 2.3 (J = 7 Hz; $H_a$), a 4-proton narrow multiplet at 2.46 ($H_b$), a broad 1-proton quartet with additional splitting at 2.88 (J = 7 Hz, $H_c$), and a 1-proton doublet with addition splitting at 5.37 (J = 3 Hz, $H_d$). Proton $H_a$ exhibited only five lines of the theoretical septet, probably as a result of the very low intensity of outer septet lines and the low S/N ratio encountered in microcell techniques.

To further characterize the compound, a reaction with p-toluenesulfonic acid was run in an attempt to produce the known ketone of Huang, et. al., shown in Table I. Example III shows the experimental details of this conversion reaction.

EXAMPLE III

Conversion of MICO To 2-Methyl-4-Isopropylcyclohex-2-En-1-One

A mixture of MICO (4.4 mg, $2.9 \times 10^{-2}$ mmol), a trace of p-toluenesulfonic acid monohydrate and $CHCl_3$ (3 mL) was refluxed for 30 min, taken up in 30 mL of ether and worked up as previously described for the $ZnBr_2$ rearrangement to yield an oily residue. One major product (>95% of total volatiles) was isolated by VPC and shown to be the desired -2-en- analog by comparison of IR and MS spectra with those of authentic materials. UV (95% EtOH) lambda(max) = 227 nm; IR 2950, 1680 (C=O), 1355 and 1375(d), 1125, 1103, 1072(d). MS m/e (rel abundance) 153(9), 152(57), 137(9), 111(10), 110(100), 109(58), 97(23), 96(19), 95(73), 81(43).

TABLE II
2,3-EPOXYCARANE REARRANGEMENT PRODUCTS

| Compound | Structure Determined by | Area Percent a | | |
|---|---|---|---|---|
| | | b | c | d |
| alpha-Terpinene | MS | 0.1 | 0.4 | 0.4 |
| Limonene | MS | 1.9 | .4 | 1.1 |
| a p-Menthatriene - possibly 1,4,8-p-menthatriene | MS | 0.2 | .4 | <0.1 |
| beta-Phellandrene and a p-menthatriene | MS | 0.6 | .4 | <0.1 |
| p-Cymene | IR & MS | 17.0 | 17.0 | 24.2 |
| Terpinolene | IR & MS | 6.0 | 0.5 | 0.1 |
| Aldehyde (probably aldehyde 5) | MS | 0.7 | <0.1 | <0.1 |
| -p,alpha-Dimethylstyrene | IR, NMR & MS | 7.7 | 22.7 | <0.5 |
| 2-Methyl-4-isopropylcyclohex-3-en-1-one mico | See Example II | 40.4 | 29.1 | 17.1 |
| Percent of total volatiles identified | | 74.4 | 70.9 | 43.4 | a - VPC peak area as a percent of total peak area
b - ZnBr$_2$ - Refluxing Toluene
c - ZnBr$_2$ - Refluxing Benzene
d - = 2% SiCl$_4$ in Benzene cooled in ice bath.

While not intending to be bound by any particular reaction mechanism theory, formation of the major product, MICO, can be postulated by a mechanism outlined in Scheme I.

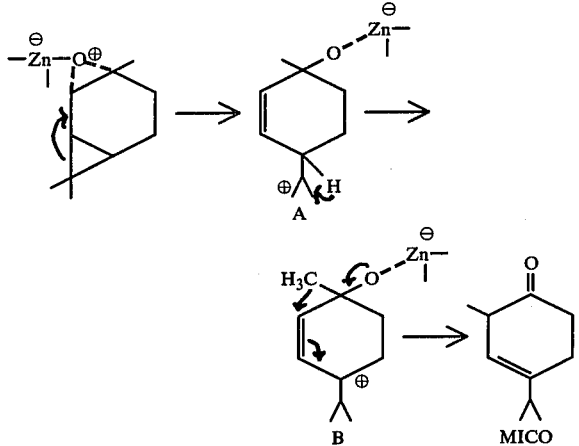

Anti-Markovnikov opening of the epoxide ring with cyclopropyl participation could yield carbonium ion A. In the previous studies by Bledsoe, et. al., Ohloff, et. al., and Arata, et. al., (above), this ion could account for the reported products without carbon rearrangement. However, by employing conventional Lewis acids (ZnBr$_2$ and SiCl$_4$), it appears that a fundamental rearrangement involving both a hydride and methyl shift takes place (A→B→MICO). The stereochemistry of the oxide and resulting carbonium ions is most likely as shown since the stereochemistry of the starting oxide, prepared with peracid, has been shown to be trans (1) by Arbuzov, et. al., IZV. Akad. Nauk, SSSR, Ser. Khim., 2163 (1969).

The methyl ketone D, which could be formed from ion B by ring migration, was not detected in the reaction mixture. In contrast, a mixture of cis- and trans-limonene oxide (7) was found by Settine, et. al., J. Org. Chem., 29, 616 (1964)) to undergo rearrangement without methyl migration but with ring contraction (7→8). Models show that these results can be explained by stereochemical differences since the axial methyl group is ideally disposed for migration (axial and parallel to the p-orbitals of the double bond) in intermediates (A, B) leading to MICO.

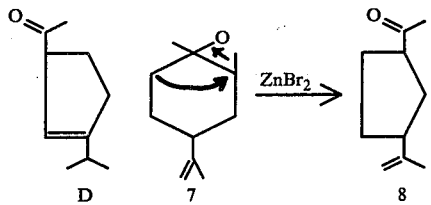

For limonene oxide (7), both the methyl group and ring carbon are equally disposed stereochemically to migration. If it is assumed that the transition state resembles the ground state, then the group with the higher migratory aptitude (the secondary ring carbon) would be expected to undergo rearrangement.

A comparison of the instrumental analyses for MICO reported herein with those reported by Kraus and Zartner (above) for their compound reveals several differences. Thus while the 100 MHZ NMR of the MICO product disclosed herein shows six distinct groups of peaks including a six-proton doublet (J = 7 Hz, CH$_3$—C—CH$_3$) and a three-proton doublet (J = 7 Hz, CH$_3$—C) cleanly separated as theoretically predicted, the disclosed 60 MHZ NMR of the Kraus and Zartner product shows a nine-proton doublet (J = 6 Hz, C—CH$_3$ and CH$_3$—C—CH$_3$). Furthermore, while the infrared spectrum of the MICO product disclosed herein shows no major peak between 1470 and 1720 reciprocal centimeters, Kraus and Zartner report an IR peak at 1645 reciprocal centimeters which they attribute to ethylenic unsaturation and a saturated carbonyl at 1750 reciprocal centimeters. There also appear to be differences between the NMR data reported in the Kraus and Zartner paper and the NMR reported in the Zartner dissertation (on which the paper was apparently based). In the dissertation, the NMR was run in carbon disulfide and reported as exhibiting a 1-hydrogen multiplet at tau=4.2–4.42 (H(on C-3)) and a 15-hydrogen multiplet at tau=7.58–9.2 (CH$_3$ on C-2, C-7, H(on C-2), H(on C-5), H(on C-6) and (H on C-7). Beyond the differences in instruments, solvents, and perhaps analytical techniques, no satisfactory explanation can be postulated for the differences in the characterizing data for MICO reported by Kraus and Zartner and those reported herein, especially in light of the successful confirmatory conversion of MICO to the known compound 2-methyl-4-isopropylcyclohex-2-en-1-one, described in Example III above.

As will be recognized by those skilled in the art, the process for producing the product ketone is applicable over a broad range of temperatures and reaction solvents. Although the yield was found to be approximately 40% (of the volatiles) in the optimum embodiment using refluxing toluene (approximately 110° C), yields for several experiments using zinc bromide in refluxing toluene under very similar conditions were found to vary unexplainably to as low as about 20%. When refluxing benzene was used (approximately 80° C) the maximum yield was approximately 30%, and, when the reaction was run at 5° C in benzene with tin tetrachloride, the yield approached 20%.

As will be recognized by those skilled in the art, the reactivities of specific Lewis acids will vary depending both on their inherent affinity for electron pair acceptance, i.e., their "hard" or "soft" character, and on the specific interaction called for in a synthesis, including a consideration of the "hardness" or "softness" of the Lewis base. In addition, the physical form of the Lewis acid in a specific reaction will bear on its effectiveness and mandate the choice of the physical parameters such as time, temperature and solvent polarity of the specific reaction. For these reasons, the highly effective Lewis acids are characteristically used at lower temperatures in solvents which are conducive to acting as reaction media at such temperatures. Boron trifluoride, for instance, is commonly used in a reaction media containing diethyl ether. For similar reasons, the reactivity of the liquid tin tetrachloride is sufficiently greater than that of dispersed solid zinc bromide that it is not surprising that the former is utilized in the instant rearrangement at approximately 5° C whereas the latter is most effective at elevated temperatures. Those skilled in the art will readily understand that the selection of the Lewis acid, the reaction time and temperature, and the solvent are related variables which are chosen in accordance with these well known principles. Given these factors, it will be understood that the reaction temperature can be broadly varied from about 0° C to about 130° C or even beyond this range but that a range of from about 80° C to about 110° C should be preferred with zinc bromide to maximize the yield of the product ketone, and that, while benzene or toluene is considered the optimum solvent for the process, organic solvents which are inert to products and reactants are broadly useful and, therefore, inert solvents such as diethyl ether and $C_5$ through $C_8$ alkanes are included in the category of preferred solvents.

Furthermore, while the Examples cited herein have used the Lewis acids zinc bromide and stannic chloride, it does not appear that the use of other Lewis acids such as aluminum chloride, boran trifluoride, etc., should fail to catalyze the reaction. It is believed that any of the above or other common Lewis acids would broadly catalyze the rearrangement of 2,3- epoxycarane to the product ketone, but that either $ZnBr_2$ or $SnCl_4$ is preferred.

Finally, while the Examples disclosed have used 2,3-carene due to its relative ease of availability, it will be apparent to those skilled in the art that various positions on the 2,3-carene skeleton may be alkylated without affecting the basic reactivity patterns which characterize the process. Most readily perceived as lacking in criticality are the hydrogen positions on carbons 5 and 6 of the carene skeleton. None of the four substituents on the 5 and 6 carbons is involved in the proposed mechanism or even close to the reactive sites. Their remoteness from the reactive sites would allow the substitution of a lower alkyl from methyl to t-butyl, phenyl, cyclohexyl or a 5,6 fused 6-member ring (one only due to attendant bond strain) at all or any combination of the four positions available on carbons 5 and 6 without negatively affecting the proposed transition state carbonium ion. Similarly, it is believed that the substitution of an ethyl, n-propyl or i-propyl group for the methyl group on carbon 1 would have no negative effect on the migration of that substituent to carbon 2 during the reaction. In fact, such a substitution may enhance the migration due to the greater migratory aptitude of these substituents in activated complex B (above) during the migration. Lastly, the two methyl groups pendant from the cyclopropyl group on the 2,3-carene skeleton appear to be relatively remote and isolated from the points of both Lewis acid attack on the epoxide and of methyl migration to allow the substitution of ethyl, n-propyl or isopropyl substituents therefore. Thus it is believed that, while 2,3-carene is the most readily available starting material for the Lewis acid catalyzed rearrangement process described hereinabove, any analog of the structural formula

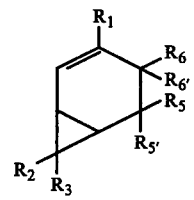

wherein $R_5$, $R_5'$, $R_6$ and $R_6'$ are selected from the group consisting of hydrogen, methyl, ethyl, n-propyl, isopropyl, n-butyl, isobutyl or t-butyl, phenyl, cyclohexyl or a 5,6 fused 6-member ring, and wherein $R_1$, $R_2$ and $R_3$ are selected from the group consisting of methyl, ethyl, n-propyl and isopropyl, would be broadly operative in the rearrangement process herein described and would be expected to exhibit fragrance characteristics sufficient to have utility in odorant compositions.

It is intended that various changes in the details, materials, steps and relative percentages which have been described may be made by those skilled in the art within the principle and scope of the invention as expressed in the appended claims. The foregoing description is considered to be only exemplary of the invention as defined in the appended claims.

We claim:

1. A process for the production of a cyclohex-3-en-1-one of the formula

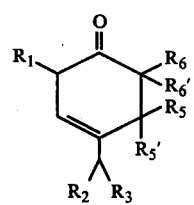

comprising contacting at a temperature of from about 0° C to about 130° C an epoxy compound of the formula

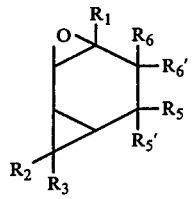

wherein $R_1$, $R_2$ and $R_3$ are selected from the group consisting of methyl, ethyl, n-propyl and isopropyl, and where $R_5$, $R_5'$, $R_6$ and $R_6'$ are selected from the group consisting of hydrogen, methyl, ethyl, n-propyl, isopropyl, n-butyl, isobutyl and t-butyl, phenyl, cyclohexyl and a 5,6 fused six membered ring, in a dry inert organic solvent with an effective amount of a Lewis acid for a time sufficient to produce said cyclohex-3-en-1-one having $R_1$, $R_2$, $R_3$, $R_5$, $R_5'$, $R_6$ and $R_6'$ substituents identical to those selected for said epoxy compound.

2. The process as set forth in claim 1 wherein contacting comprises:
  (a) dissolving said epoxy compound in a first portion of said solvent to form a first reactant mixture;
  (b) mixing said Lewis acid in a second portion of said solvent to form a second reactant mixture; and
  (c) adding said first and said second reactant mixtures together to form a reaction mixture.

3. The process as set forth in claim 2 additionally comprising purifying said cyclohex-3-en-1-one.

4. The process as set forth in claim 3 wherein dissolving additionally comprises providing said epoxy compound in an amount sufficient to produce a concentration of from about 1 to about 20 wt.% of said epoxy compound in said first reactant solution and wherein mixing additionally comprises providing said Lewis acid in an amount sufficient to produce from about 100 to about 20 fold mole excess of epoxy compound over Lewis acid in said reaction mixture.

5. The process as set forth in claim 4 wherein adding comprises admixing said first reactant solution to said second solution.

6. The process as set forth in claim 5 wherein purifying comprises:
  (a) washing said reaction mixture with a series of aqueous solutions to remove water soluble components of said reaction mixture; and
  (b) separating said cyclohex-3-en-1-one from the washed reaction mixture.

7. The process as set forth in claim 6 wherein separating comprises:
  (a) drying said washed reaction mixture;
  (b) thermally removing a portion of said solvent to give a product mixture; and
  (c) fractionating said product mixture to isolate said cyclohex-3-en-1-one.

8. The process as set forth in claim 7 wherein fractionating comprises injecting said product mixture into a vapor phase chromatography apparatus and collecting said cyclohex-3-en-1-one as eluted from said apparatus.

9. The process as set forth in claim 8 wherein washing comprises successively washing said reactant mixture with two volumes of water, one volume of saturated aqueous sodium bicarbonate and one volume of saturated aqueous sodium chloride, and wherein said volumes are calculated to be not greater than that of said reaction mixture.

10. The process as set forth in claim 9 additionally comprising taking up said reaction mixture in from about a 3-fold to about a 10-fold volume excess of a readily removable, movable, compatible organic solvent prior to said successively washing.

11. The process as set forth in claim 10 wherein drying comprises exposing said washed reaction mixture to anhydrous sodium sulfate in an amount and for a time, sufficient to dry said washed reaction mixture.

12. A process for the production of a cyclohex-3-en-1-one of the formula

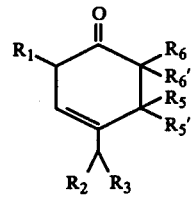

comprising:
  (a) dissolving a sufficient amount of an epoxy compound of the formula

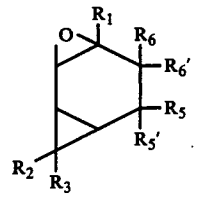

wherein $R_1$, $R_2$ and $R_3$ are selected from the group consisting of methyl and ethyl and $R_5$, $R_{5'}$, $R_6$ and $R_{6'}$ are selected from the group consisting of hydrogen, methyl and ethyl, in a first dry, inert organic solvent to form a first reactant mixture having a concentration of from 1–20 wt.% in said epoxide compound;
  (b) mixing a sufficient amount of a Lewis acid in said first, dry, inert organic solvent to form a second reactant mixture having a molar concentration of said Lewis acid of from about 1 to about 20 percent of that for said epoxide compound in said first reactant mixture;
  (c) adding said first reactant mixture to said second reactant mixture to form a reaction mixture;
  (d) allowing said epoxide compound and said Lewis acid in said reaction mixture to react to form said cyclohex-3-en-1-one;
  (e) taking up said reacted reaction mixture in from about a 3-fold to about a 10-fold excess of a readily removable, compatible second organic solvent;
  (f) washing the diluted reaction mixture with a water solution to remove water soluble components;
  (g) drying said washed reaction mixture; and
  (h) separating said cyclohex-3-en-1-one from other components of said reaction mixture.

13. The process as set forth in claim 12 wherein washing comprises successively washing said reaction mixture with two volumes of water, one volume of saturated sodium bicarbonate and one volume of saturated sodium chloride, and wherein said volumes are calculated to be not greater than that of said reaction mixture.

14. The process as set forth in claim 13 wherein separating comprises:

(a) distilling a portion of said first and said second solvent from said reaction mixture to give a concentrated product mixture; and
(b) fractionating said concentrated product mixture chromatographically to yield purified said cyclohex-3-en-1-one.

15. The process as set forth in claim 14 additionally comprising selecting said Lewis acid from the group consisting of aluminum trichloride, boron trifluoride, tin (IV) tetrachloride, zinc chloride and, zinc bromide.

16. The process as set forth in claim 15 additionally comprising restricting said first organic solvent to a dry, inert solvent.

17. The process as set forth in claim 16 wherein said dry inert solvent is selected from the group consisting of diethyl ether, $C_5$ to $C_8$ alkanes, benzene and toluene.

18. The process as set forth in claim 17 wherein said Lewis acid is zinc bromide and additionally comprising maintaining said reaction mixture at a temperature of from about 80° C to about 110° C immediately after adding said first reactant mixture to said second reactant mixture.

19. The process as set forth in claim 18, additionally comprising heating said second reactant mixture to a temperature of from about 80° C to about 110° C, vigorously stirring said heated second reactant mixture to disperse said zinc bromide, and wherein said adding is done at a rate sufficiently slow to minimize the temperature change caused by said adding.

20. The process as set forth in claim 16 wherein said Lewis acid is stannic chloride, said first solvent is benzene and wherein the temperature of said reaction mixture is not greater than about 5° C.

21. A process for the production of 2-methyl-4-isopropylcyclohex-3-en-1-one comprising:
(a) providing 2,3 epoxycarane;
(b) dissolving said 2,3 epoxycarane in a sufficient amount of a dry, inert solvent to form a first reactant mixture having a concentration of from about 1 to about 20 wt.% of said 2,3 epoxycarane;
(c) mixing a sufficient amount of a Lewis acid in said first, dry, inert hydrocarbon solvent to form a second reactant mixture having a molar concentration of said Lewis acid of from about 1 to about 20% of that for said 2,3 epoxycarane in said first reactant mixture;
(d) adding said first reactant mixture and said second reactant mixture together to form a reaction mixture;
(e) allowing said 2,3 epoxycarane and said Lewis acid reaction mixture to interact for a time sufficient to form said 2-methyl-4-isopropylcyclohex-3-en-1-one product;
(f) taking up said reaction mixture containing said product in a 3 to 10-fold excess of a second inert solvent;
(g) extracting water-soluble components from said reaction mixture by washing with an aqueous solution;
(h) drying said washed reaction mixture; and
(i) separating said 2-methyl-4-isopropylcyclohex-3-en-1-one from other components of said reaction mixture.

22. The process as set forth in claim 21 wherein said Lewis acid is selected from the group consisting of aluminum trichloride, boron trifluoride, tin tetrachloride and zinc bromide.

23. The process as set forth in claim 22 wherein said first and said second inert solvents are selected from the group consisting of toluene, benzene, diethyl ether, and $C_5$–$C_8$ alkanes.

24. The process as set forth in claim 23 wherein said first solvent is toluene and said Lewis acid is zinc bromide.

25. The process as set forth in claim 23 wherein said first solvent is benzene and said Lewis acid is zinc bromide.

26. The process as set forth in claim 23 wherein said first solvent is benzene and said Lewis acid is tin tetrachloride.

27. The process as set forth in claim 24 additionally comprising heating said second reactant mixture to reflux prior to said adding.

28. The process as set forth in claim 27 wherein adding comprises admixing said first reactant mixture to said second reactant mixture such that said temperature of said second solution is maintained proximate to the reflux temperature.

29. The process as set forth in claim 25 additionally comprising heating said second reactant mixture to reflux prior to said adding and wherein adding comprises admixing said first reactant mixture to said second reactant mixture at a rate such that the temperature of said reaction mixture is maintained proximate to reflux.

30. The process as set forth in claim 25 additionally comprising cooling one of said reactant mixtures to a temperature not greater than about 10° C and wherein adding comprises admixing the other said reactant mixture with said cooled reactant mixture at a rate such that the temperature of said reaction mixture is maintained at not greater than about 10° C.

31. The process as set forth in claim 21 wherein providing comprises epoxidizing 2,3 carene.

32. The process as set forth in claim 31 wherein epoxidizing comprises:
(a) treating 2,3 carene with an excess of m-chloroperbenzoic acid at a temperature not greater than 10° C for about 1–2 hours to form an epoxidation solution;
(b) raising the temperature of said epoxidation solution to ambient for about 1–2 hours;
(c) removing water soluble components from said epoxidation solution; and
(d) concentrating said dried epoxidation solution to yield 2,3 epoxycarane.

33. A process for the production of 2-methyl-4-isopropylcyclohex-3-en-1-one from 2,3 epoxycarane comprising contacting said 2,3 epoxycarane with a Lewis acid selected from the group consisting of aluminum chloride, boron trifluoride, tin tetrachloride and zinc bromide in a dry, inert solvent for a time sufficient to produce said 2-methyl-4-isopropylcyclohex-3-en-1-one.

34. The process as set forth in claim 33 wherein said Lewis acid is zinc bromide or tin tetrachloride.

35. The process as set forth in claim 34 wherein said solvent is benzene or toluene.

* * * * *